(12) United States Patent
Sung et al.

(10) Patent No.: US 9,575,015 B2
(45) Date of Patent: Feb. 21, 2017

(54) SYSTEMS AND METHODS FOR X-RAY PHASE CONTRAST IMAGING USING ARRAYS OF X-RAY FOCUSING ELEMENTS

(71) Applicants: Yongjin Sung, Boston, MA (US); Rajiv Gupta, Wayland, MA (US)

(72) Inventors: Yongjin Sung, Boston, MA (US); Rajiv Gupta, Wayland, MA (US)

(73) Assignee: The General Hospital Corporation, Boston, MA (US)

( * ) Notice: Subject to any disclaimer, the term of this patent is extended or adjusted under 35 U.S.C. 154(b) by 136 days.

(21) Appl. No.: 14/673,304

(22) Filed: Mar. 30, 2015

(65) Prior Publication Data

US 2015/0340113 A1    Nov. 26, 2015

Related U.S. Application Data

(60) Provisional application No. 61/972,856, filed on Mar. 31, 2014.

(51) Int. Cl.
  *G01N 23/04* (2006.01)
  *G21K 1/06* (2006.01)
  *G01N 23/20* (2006.01)

(52) U.S. Cl.
  CPC ........ *G01N 23/04* (2013.01); *G01N 23/20075* (2013.01); *G21K 1/06* (2013.01);
  (Continued)

(58) Field of Classification Search
  CPC .............. G01N 2223/303; G01N 23/04; G01N 23/20075; G01N 23/046; G01N 2223/419; G01N 2223/423; G01N 2223/076; G01N 2223/1003; G01N 2223/6126; G01N 23/223; G01N 2223/315; G01N 23/02; G01N 23/20008; G01N 2223/313; G01N 2223/401; G21K 1/06; G21K 2201/067; G21K 2207/005; A61B 6/583; A61B 6/032; A61B 6/4021; A61B 6/027; A61B 6/12; A61B 5/06; A61B 2090/376; A61B 6/4441; A61B 34/20; A61B 6/4291; A61B 6/547; A61B 90/36; A61B 2034/2051; A61B 6/06; A61B 6/587; A61B 2017/00725; A61B 6/00
  (Continued)

(56) References Cited

U.S. PATENT DOCUMENTS

| | | | | |
|---|---|---|---|---|
| 5,812,629 A | * | 9/1998 | Clauser | ................. A61B 6/032 378/37 |
| 2007/0140438 A1 | * | 6/2007 | Horndler | ................. A61B 6/12 378/207 |

(Continued)

*Primary Examiner* — Irakli Kiknadze
(74) *Attorney, Agent, or Firm* — Quarles & Brady LLP

(57) ABSTRACT

Systems and methods for performing x-ray phase-contrast imaging using a conventional x-ray source and detector are provided. An array of x-ray focusing elements it provided and used to focus x-ray onto a pattern of multiple different focal spots. When an object is introduced into the beam path, the focal spots will be displaced based on the x-rays being refracted by the object. A refraction angle map is produced and used to generate a phase contrast image, such as an image that indicates the electron density distribution in the object. Multi-spectral imaging can be achieved by utilizing the chromatic aberration of the array of x-ray focusing elements and sweeping the detector through different focal planes associated with different x-ray energy levels or sweeping the peak voltage of the x-ray source for a fixed object-to-detector distance.

24 Claims, 7 Drawing Sheets

(52) U.S. Cl.
CPC . *G01N 2223/303* (2013.01); *G21K 2201/067* (2013.01); *G21K 2207/005* (2013.01)

(58) Field of Classification Search
USPC .. 378/4, 19, 20, 8, 154, 37, 207; 250/370.1; 382/128, 130–132
See application file for complete search history.

(56) References Cited

U.S. PATENT DOCUMENTS

| | | | | |
|---|---|---|---|---|
| 2007/0274457 | A1* | 11/2007 | Dunham | A61B 6/032 378/207 |
| 2010/0061506 | A1* | 3/2010 | Koehler | A61B 6/022 378/19 |
| 2011/0176663 | A1* | 7/2011 | Shaughnessy | A61B 6/032 378/154 |
| 2013/0182820 | A1* | 7/2013 | Proksa | A61B 6/032 378/8 |
| 2014/0126688 | A1* | 5/2014 | Flohr | G01N 23/046 378/19 |

* cited by examiner

SYSTEMS AND METHODS FOR X-RAY PHASE CONTRAST IMAGING USING ARRAYS OF X-RAY FOCUSING ELEMENTS

CROSS-REFERENCE TO RELATED APPLICATIONS

This application claims the benefit of U.S. Provisional Patent Application Ser. No. 61/972,856, filed on Mar. 31, 2014, and entitled "SYSTEMS AND METHODS FOR X-RAY PHASE CONTRAST IMAGING USING ARRAYS OF X-RAY FOCUSING ELEMENTS."

STATEMENT REGARDING FEDERALLY SPONSORED RESEARCH

This invention was made with government support under N66001-11-4204 awarded by the Defense Advanced Research Projects Agency. The government has certain rights in the invention.

BACKGROUND OF THE INVENTION

The field of the invention is systems and methods for x-ray phase contrast imaging. More particularly, the invention relates to systems and methods for performing x-ray phase contrast imaging using conventional x-ray sources and detectors.

X-rays have been widely used in medical imaging since their discovery in 1895. In medical x-ray imaging, these relatively energetic photons interact with body parts that have different attenuating properties to generate contrast for visualization of the difference between organs. Microscopically, the interaction between x-ray photons and tissue is described by different photon cross-sections due to physical processes such as photoelectric absorption, Thomson scattering, Compton scattering, and pair production. In the diagnostic x-ray energy range (10 keV-150 keV), the pair production can be ignored.

Conventional x-ray systems, such as computed tomography ("CT") systems, record the attenuation of x-rays due to photoelectric and Compton effects, while regarding the refraction or the angular deviation due to Thomson and Compton scattering as sources of noise. Because the attenuation parameters are very similar in low-atomic-number ("low-Z") materials, such as soft tissues, these systems cannot adequately differentiate those materials from each other. For instance, absorption-based CT images typically do not effectively distinguish tumors from surrounding healthy tissues.

To overcome this limitation, x-ray phase contrast imaging methods have been developed. When x-rays pass through an object they are not only attenuated, but also experience local phase shifts based on differences in the electron density throughout the object. These local phase shifts can be measured and used as a basis of a contrast mechanism that produces significantly better contrast-to-noise ratio ("CNR") compared to conventional CT imaging when imaging soft tissues. X-ray phase contrast imaging is thus particularly effective for imaging low-Z materials (e.g., soft tissues or improvised explosives) that have similar attenuation properties.

Although x-ray phase contrast imaging provides significant improvements in the CNR achievable for low-atomic-number materials, its practical implementation has been limited by hardware constraints. Typically, x-ray phase contrast imaging methods require an x-ray source with a high degree of spatial and temporal coherence; namely, a small focal spot size and narrow spectral bandwidth. As a result, x-ray sources used in conventional x-ray imaging systems, such as those used in current clinical practice, are not suitable for phase contrast imaging. Instead, the majority of x-ray phase contrast imaging is performed using an x-ray synchrotron radiation source, which is not practical due to its size and cost, or using a micro-focus source that is too weak to be used for medical imaging applications.

Recently, some methods for performing x-ray phase contrast imaging using a conventional x-ray source have been proposed. For example, in a method called Talbot interferometry, a series of periodic gratings is used, in which one absorption grating is put right in front of the source to increase the spatial coherence of x-rays and two other gratings are put in the imaging chain to record the phase effect. This system requires a careful alignment of the gratings, however, which makes the system not suitable for applications in the field. More importantly, this system is very challenging to scale the size of system up to one that is applicable for scanning a human subject. The difficulty with scaling the Talbot interferometry system is because the thickness of the gratings has to increase as the size of the imaged object increases; however, a thick grating will not allow x-rays to pass through except in the region very close to the center.

In another recently proposed method called spatial harmonic imaging, an image of a two-dimensional periodic structure, such as a wire mesh, is acquired using a high-resolution detector. The local displacement of the image after inserting an object in the imaging chain is connected to the phase shift of x-rays due to the object. This system, however, requires the pixel size of detector to be very small (e.g., on the order of 10 micron), which cannot be adapted in a clinical imaging setting. In addition, the CNR decreases rapidly as the size of the imaged object increases.

In light of these issues, there remains a desire to provide systems and methods for performing x-ray phase contrast imaging at a human scale while using a conventional x-ray source and detector.

SUMMARY OF THE INVENTION

The present invention overcomes the aforementioned drawbacks by providing systems and methods for x-ray phase contrast imaging using conventional x-ray sources and detectors together with one or more arrays of x-ray focusing elements ("XFEs") positioned between the object being imaged and the x-ray detector.

It is an aspect of the invention to provide a method for x-ray phase contrast imaging using an x-ray imaging system. The method may include acquiring an image of an object using an x-ray imaging system that includes an x-ray source, an x-ray detector, and an array of x-ray focusing elements. The array of x-ray focusing elements are positioned between the x-ray source and the x-ray detector and configured to focus x-rays incident on the array of x-ray focusing elements onto a pattern of focal spots on the x-ray detector. The array of x-ray focusing elements may be positioned between the x-ray source and the object, or between the object and the x-ray detector. The image acquired with the x-ray imaging system while the object is positioned in the x-ray imaging system is indicative of a displacement of the focal spots based on a refraction of x-rays by the object. A calibration image that depicts the pattern of focal spots defined by the array of x-ray focusing elements is provided. A refraction angle map that indicates a refraction angle associated with each focal spot is then produced. This refraction angle map is based on the displacement of the focal spots measured using the acquired image and the calibration image. An image of the object that is indicative an electron density distribution in the object is then produced based on refraction angle maps obtained for varying angles of illumination of x-rays onto the object.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
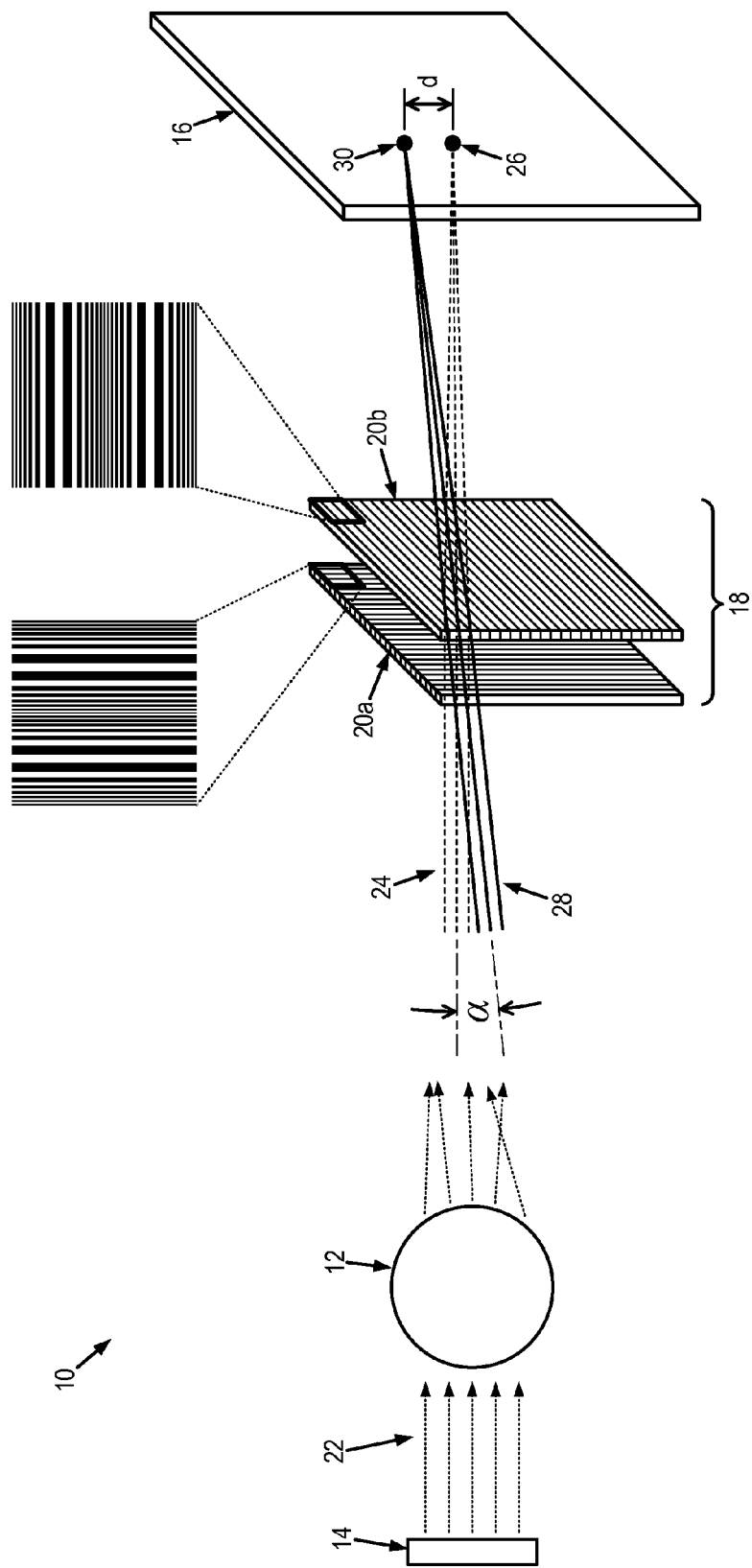
FIG. 1 is an example of an x-ray imaging system that incorporates an array of x-ray focusing elements ("XFEs") to focus x-rays onto a pattern of multiple different x-ray focal spots, the array of XFEs in the illustrated example including two linear zone-plate arrays arranged orthogonal to each other.

Described here are systems and methods for performing x-ray phase-contrast imaging using a conventional x-ray source and detector. To achieve this with a conventional x-ray source and detector, one or more arrays of small, x-ray focusing elements ("XFEs") are positioned between the object being imaged and the x-ray detector. As an example, an array of XFEs may include a zone-plate array or an array of photon sieves. As still another example, an XFE may be composed of one or more crystalline silicon wafers with inter-plane distances matched with the wavelengths of the x-rays generated by an x-ray source used when imaging an object.

The systems and methods described here are capable of generating x-ray phase contrast images by inserting an array of XFEs into the imaging chain of currently available x-ray imaging systems, such as those that acquire x-ray attenuation data using a broadband x-ray spectrum (e.g., small temporal bandwidth) and large focal spot (e.g., small spatial coherence). In some embodiments, the array of XFEs can be inserted into the imaging chain by positioning the array of XFEs between the x-ray source and the object. In some other embodiments, the array of XFEs can be inserted into the imaging chain by positioning the array of XFEs between the object and the x-ray detector. Because a conventional x-ray source can be used with this technique, a higher signal-to-noise ratio ("SNR") than is achievable with other phase contrast imaging techniques can be obtained.

Image formation in x-ray radiography, tomography, and inspection use differences in the attenuation properties of materials as the source of image contrast. Phase contrast imaging, on the other hand, uses differences in the x-ray retardation (or phase shift) properties of a material, which are complementary to the materials' attenuation properties. As a result, high-CNR images may be formed for the low-Z materials that have very similar attenuation properties and thus cannot be easily distinguished using conventional absorption-based x-ray imaging. Because these low-Z materials have quite different phase-shift properties, however, phase contrast imaging is capable of producing images with high CNR between low-Z materials.

The behavior of x-rays as they travel through an object can be described using a complex index of refraction, as in conventional optics. In the x-ray region, the index of refraction, n, deviates only slightly from unity, where n represents the speed of the x-rays in a vacuum over the speed of the x-rays in a medium. The index of refraction can be expressed as, $$n = 1 - \delta - i\beta \quad (1);$$

where $\beta$ describes the absorption of x-rays and the phase-shift term, $\delta$, incorporates phase-shift effects. X-rays passing through regions of differing $\delta$ are pick up different relative phases and thus have a distorted wave front after passing through the object. These phase differences, or the wavefront distortion, can then be detected by various phase-contrast imaging techniques. Advantageously, because the phase contrast for low-Z materials is much higher than the absorption contrast, imaging can be conducted with a reduced dose of absorbed radiation being imparted to the patient. For example, dose can be reduced by a factor of twenty-five or more, thereby reducing potential damage to tissues.

In general, there are three categories of phase contrast imaging. These include interferometry, diffractometry, and in-line holography. The phase change introduced in incident x-rays passing through an object can be defined by integrating over the ray path as follows, $$\phi = -\frac{2\pi}{\lambda} \int \delta(s) ds; \quad (2)$$

where λ is the wavelength of x-rays. With this definition, the aforementioned categories of phase contrast imaging can be viewed as recording measurements of ϕ, ∇ϕ, and ∇²ϕ, respectively.

Based on Eqn. (2), and analogous to attenuation-based CT reconstruction, as long as the phase shift can be measured, tomographic reconstruction principles can be applied to provide the local distribution of electron density. To accomplish this, the phase shift can be measured around the object from many different view angles, and the local electron density distribution can be reconstructed using an appropriate image reconstruction algorithm.

Typically, the x-ray phase shifts are connected to other quantities that are easier to measure. As an example, the refraction angle, which is the angular deviation of the propagation direction of an exit wave from its incident propagation direction, is a measurable quantity to which phase shift can be directly related. Assuming that the x-ray wave propagates along the z-direction, the refraction phenomenon can be measured in the x-y plane, which is perpendicular to the wave propagation direction. For example, the refraction angle along the x-direction, α, is related to the phase shift as follows:

$$\alpha(x, y) = \frac{\lambda}{2\pi} \frac{\partial \phi(x, y)}{\partial x}. \quad (3)$$

This relationship has been used as a foundation in modern optics to investigate material properties. However, observation of this refraction effect for diagnostic x-rays is still very difficult because the refraction angle is on the order of micro-radians and the refracted x-rays are intermingled with each other. In past years, investigators have tried many different schemes to measure the refraction angle or its variants.

The systems and methods of the present invention are capable of measuring the refraction using a conventional x-ray source and detector. For instance, the measurement in the systems described here involves recording locations of focal spots, which are bright and intense. Thus, compared to spatial harmonic imaging, which does not use such an x-ray focusing mechanism, the system of the present invention can provide high signal-to-noise ratio. Furthermore, contrary to spatial harmonic imaging, which requires imaging a periodic structure, the present method only requires knowing the positions, such as the centroids, of x-ray focal spots and, thus, greatly relaxes the requirement of high spatial resolution. Contrary to systems that require multiple gratings (e.g., a Talbot interferometry system), the system of the present invention does not require multiple gratings that must be precisely aligned. Therefore, the systems of the present invention can be easily deployed in the field and readily scaled up to sizes that are practical for scanning human subjects. Once the local displacements of focal spots are measured, the refraction angles or the x-ray phase shifts can be determined at each point, from which phase contrast images can be produced.

Referring to FIG. 1, an example setup of an x-ray imaging system 10 that implements an array of XFEs for performing x-ray phase contrast imaging is illustrated. In this configuration, an object 12 to be imaged is positioned in the x-ray imaging system 10 between an x-ray source 14 and an x-ray detector 16. The x-ray source may be a source commonly used in conventional x-ray imaging systems (e.g., with a broad x-ray energy spectrum, large focal spot). An XFE array 18 is positioned between the object 12 and the detector 16. In the example shown in FIG. 1, the XFE array 18 includes a first zone-plate array 20a and a second zone-plate array 20b. The first zone-plate array 20a is composed of a periodic pattern of linear zones that are vertically aligned. The second zone-plate array 20b is composed of a periodic pattern of linear zones that are horizontally aligned.

Figure 2:
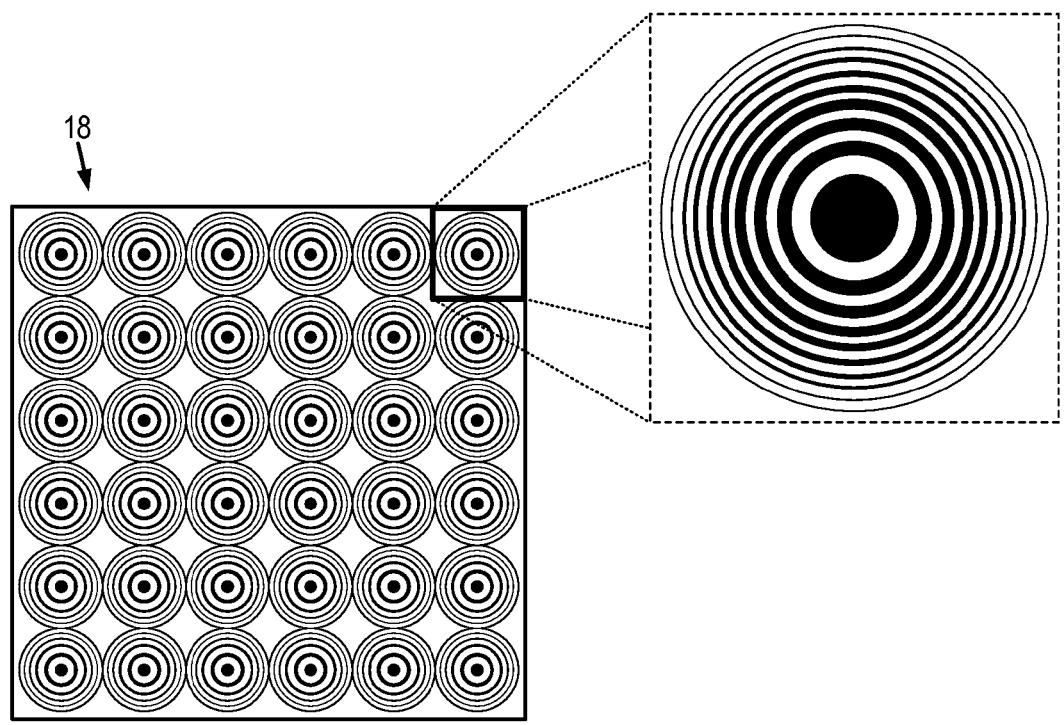
FIG. 2 is an example of an array of XFEs, in which each XFE is a radial zone-plate.
Figure 3:
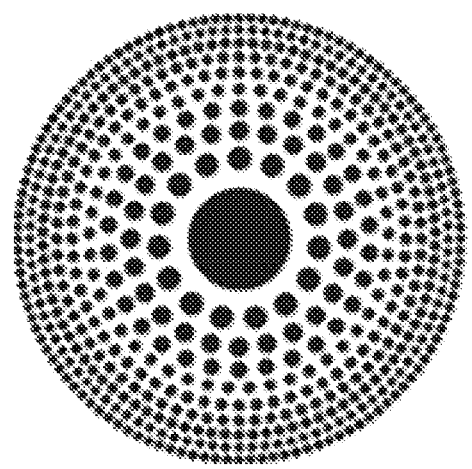
FIG. 3 is an example of a photon sieve that may be used as an XFE, an array of which would form an example of an array of such XFEs.

It will be appreciated by those skilled in the art that the XFE array 18 may incorporate any suitable number of zone-plate arrays 20 and that such zone-plate arrays 20 may be composed of zones having any number of different suitable geometries. For example, the XFE array 18 can be composed of an array of radial zone plates that each include a plurality of concentric, radially symmetric rings, as shown in FIG. 2. In still other examples, the XFE array 18 can be composed of an array of other x-ray focusing elements, such as an array of photon sieves, an example of which is shown in FIG. 3.

Thus, in some embodiments, an XFE array 18 composed of a single layer that contains two-dimensional periodic patterns can be used. In some other embodiments, an XFE 18 array may include two layers. For instance, in some two-layer configurations, each layer may contain a periodic, one-dimensional pattern.

Figure 4:
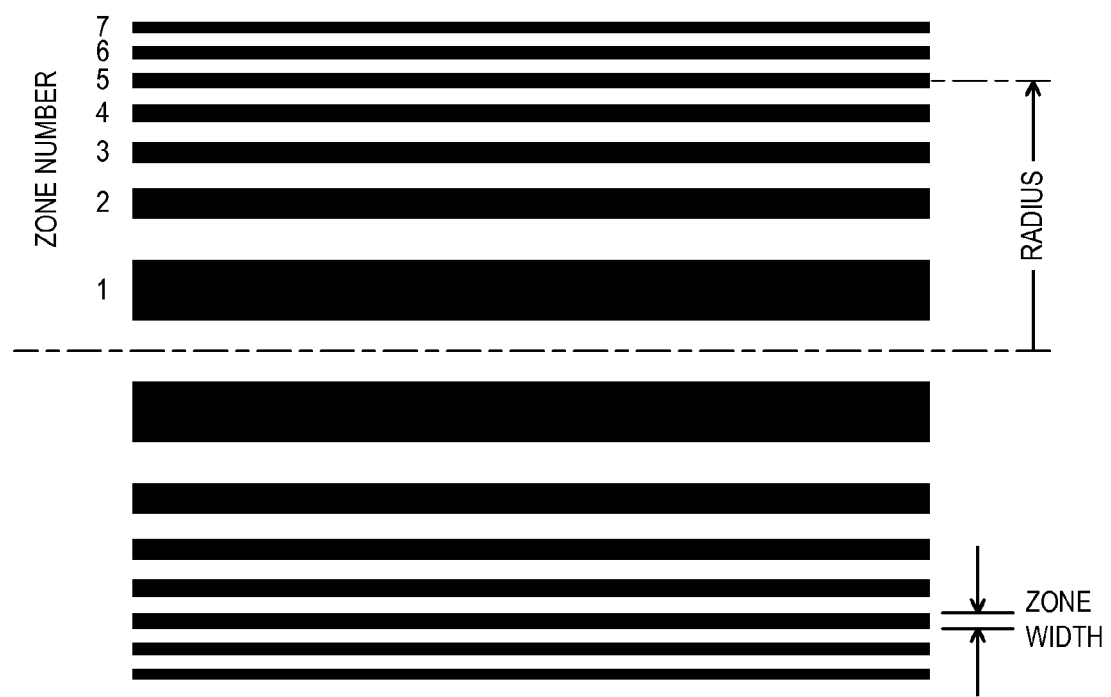
FIG. 4 is an illustrative example of an XFE that forms a part of a one-dimensional zone-plate array

The size of each x-ray focusing element in the XFE array 18 will depend on the detector pixel size, the source-to-object distance ("SOD"), and the object-to-detector ("ODD") distance. By way of example, an x-ray focusing element that forms a part of a linear zone-plate array is illustrated in FIG. 4. This x-ray focusing element includes a number of zones, identified by the zone number, spaced apart from the center of the x-ray focusing element at different distances, referred to as radii. Each zone has a zone width.

Figure 5:
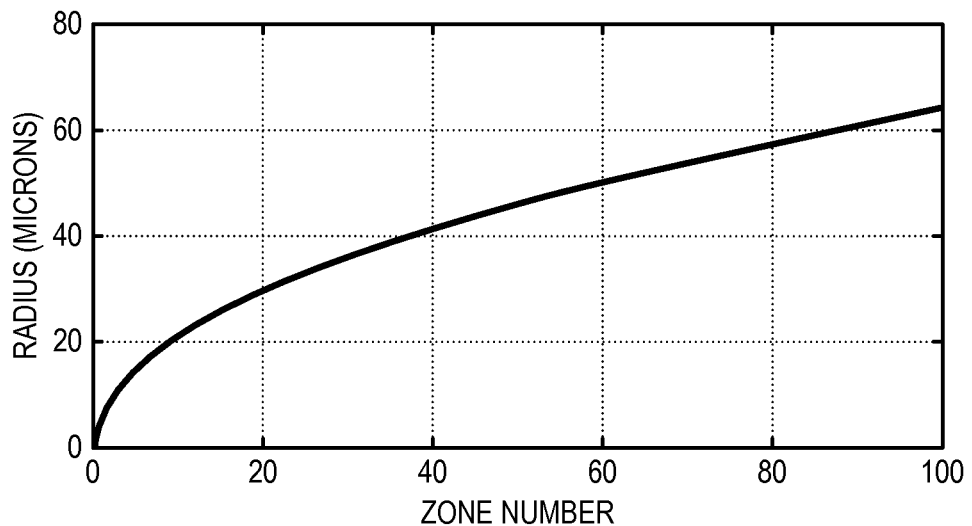
FIG. 5 is an example of a plot that illustrates the radius of each successive zone in a zone-plate array that forms a part of some embodiments of an array of XFEs.

As the zone number in an XFE increases, the radius of each successive zone preferably increases according to a nonlinear relationship. An example of such a relationship is illustrated in FIG. 5. For a linear XFE, such as those that are implemented in a linear zone-plate array, the radius is the distance from the center of the XFE to the midpoint of a particular zone, measured perpendicular to the direction along which the zone extends. For a radial XFE, the radius is the distance from the center of the XFE to the midpoint of a particular zone.

Figure 6:
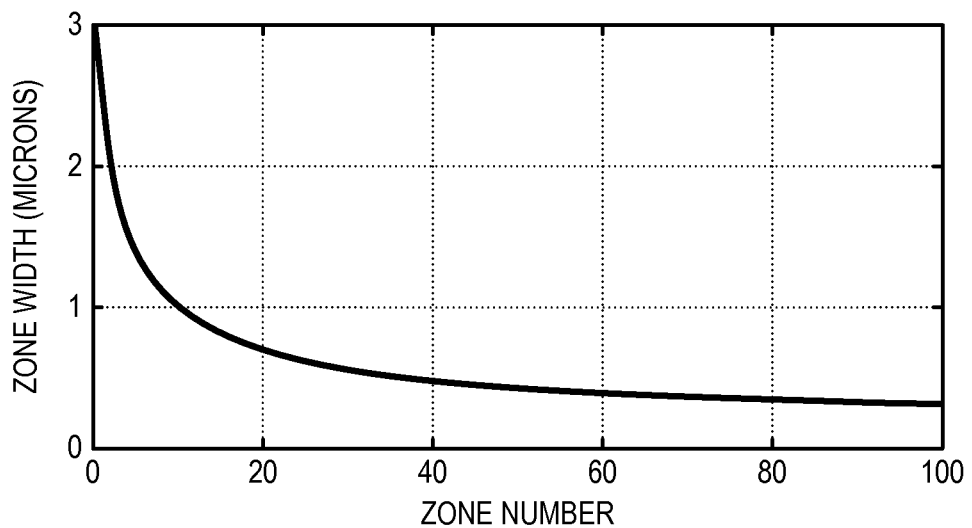
FIG. 6 is an example of a plot that illustrates the width of each successive zone in a zone-plate array that forms a part of some embodiments of an array of XFEs.

As the number of zones in an XFE increases, the zone width of each successive zone preferably decreases according to a nonlinear relationship. An example of such a relationship is illustrated in FIG. 6.

Each XFE can be made either as an absorption-type XFE or as a phase-type XFE, irrespective of whether the XFE is linear, radial, a photon sieve, or one or more crystalline silicon wafers with x-ray wavelength-matched inter-plane distances. As one example, an absorption-type XFE can be made by depositing high-Z materials (e.g., gold) on a substrate. In some embodiments, a phase-type XFE can be made by depositing low-Z materials (e.g., Beryllium) on a substrate. In some other embodiments, a phase-type XFE can be made by etching the appropriate pattern on a substrate. The focusing efficiency, and thus SNR, of the phase-type XFE is typically higher than that of absorption-type XFE.

In some embodiments, the array of XFEs can be manufactured as a single unit, while in some other embodiments, the array of XFEs can be made by assembling small units in a pattern, such as a mosaic pattern. Unlike Talbot interferometry, in which multiple gratings have to be carefully aligned, the assembling tolerance for producing an XFE array is greatly relaxed. In fact, the assembling tolerance does not affect the SNR or image quality in the present method, because the displacement of focal spots, not their absolute location, is used to generate the image.

As one example, the following specifications may be used for an XFE array for an ODD of one meter. The overall width of the XFE can be around 130 microns and can include 100 zones. The smallest zone width in this example can be around 0.3 micron. An XFE array manufactured with these specifications is contemplated to result in focal spots that are 0.4 microns in diameter. The (monochromatic) focusing efficiency of this example design is around ten percent when the XFE is constructed as an absorption-type XFE, and is around forty percent when the XFE is constructed as a phase-type XFE. The XFE arrays used in the present invention can be readily manufactured using any suitable micro-fabrication facility.

Referring again to FIG. 1, when no object 12 is positioned in the x-ray imaging system 10, the x-rays 22 generated by the x-ray source will arrive at the XFE array 18 and be focused by the XFE array 18 onto a pattern of focal spots on the detector 16. The pattern of focal spots is determined by the configuration of the XFE array 18. As an example, x-rays arriving at the XFE array 18 along beam paths 24 are focused by the XFE array 18 onto a focal spot 26 on the detector 16.

When the object 12 is positioned in the x-ray system 10, however, the object 12 will refract the x-rays so that they arrive at the XFE array 18 at different incident angles that are correlated to the local phase shifts caused by the refractive properties of the object 12. As an example, the x-rays travelling along beam paths 24 when no object 12 was present in the x-ray imaging system 10 will be refracted when they pass through the object 12 and thus will arrive at the XFE array 18 along beam paths 28 that are deflected from beam paths 24 by an angle, $\alpha$. As a result of this change in incident angle, the x-rays will be focused on a different location 30 on the detector 16 than the intended focal spot 26. The displacement, d, of the focal spot 26 to the shifted location 30 can be related to the angular shift, $\Delta\alpha$, which in turn can be related to the refractive properties of the object 12. Thus, a phase contrast image of the object 12 can be produced by acquiring an image of the object 12 and comparing the displacements of the focal spots from their intended locations and relating those displacements to the refractive properties of the object 12.

Figure 7A:
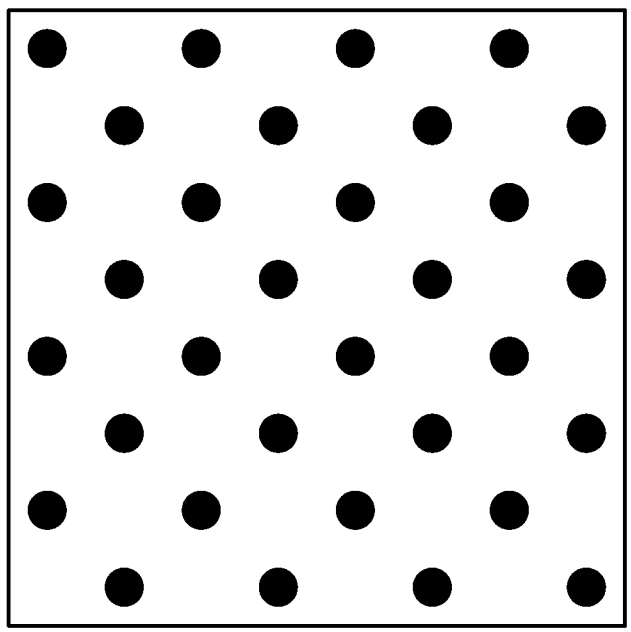
FIG. 7A is an illustrative example of the pattern of x-ray focal spots produced by an array of XFEs.
Figure 7B:
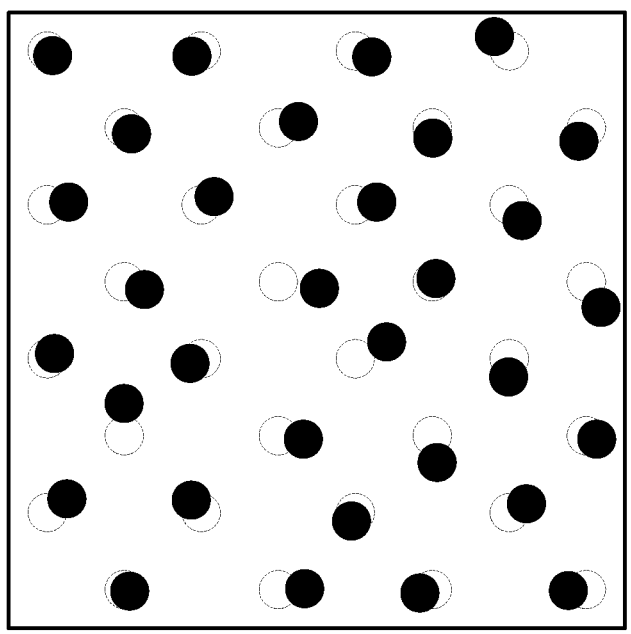
FIG. 7B is an illustrative example of the pattern of x-ray focal spots of FIG. 7A after they have been displaced by refractive effects resulting from the x-ray passing through an object before impinging on the array of XFEs.

As mentioned above, the XFE array will generate a pattern of focal points on the detector. For instance, in some embodiments the XFE array will generate a grid pattern of focal points, such as the pattern illustrated in FIG. 7A. When an object is positioned between the x-ray source and the XFE array, the focal points will be displaced based on the refraction of x-rays passing through the object, as illustrated in FIG. 7B. In general, each focused x-ray beam arriving at the detector will be displaced by an amount depending on the incident angle of the x-ray beams onto the XFE array. The incident angle of the x-ray beams changes as the beams pass through the object because of the inhomogeneous electron density distribution within the object. By recording the amount of displacement of the individual focal spots, it is possible to obtain a two-dimensional map of the projected electron density for the object. This electron density information is not available in conventional x-ray imaging, but is very useful for high-contrast soft-tissue imaging using x-ray and for non-medical imaging applications, such as explosives detection.

Figure 8:
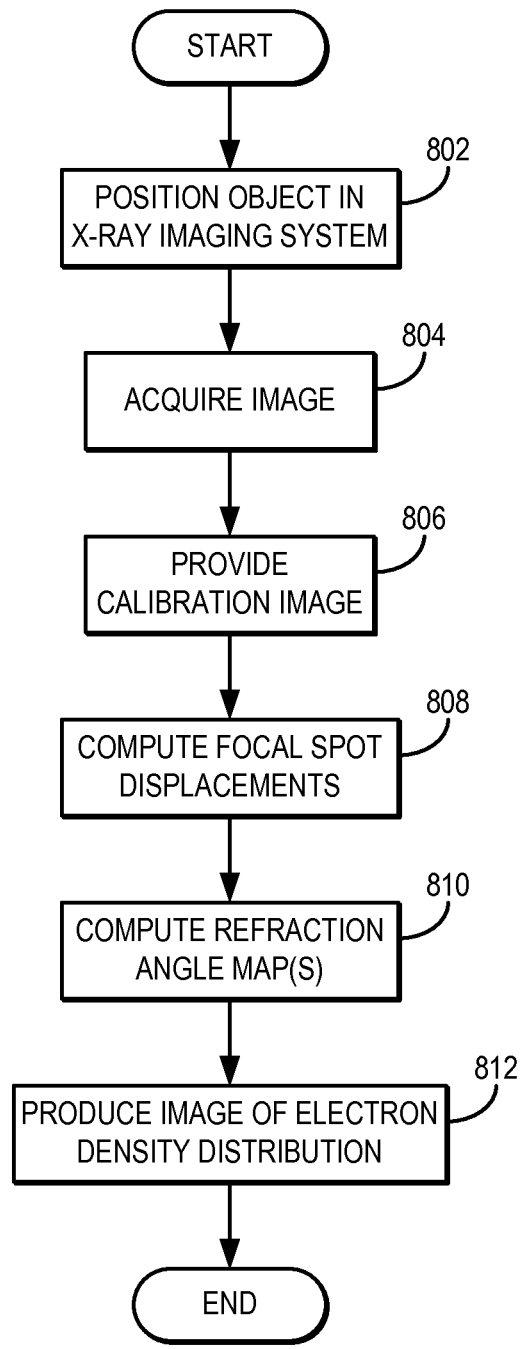
FIG. 8 is a flowchart setting forth the steps of an example of a method for performing x-ray phase contrast imaging using a conventional x-ray imaging system and an array of XFEs.

Referring now to FIG. 8, a flowchart setting forth the steps of an example of a method for performing x-ray phase contrast imaging with a conventional x-ray imaging system using one or more XFE arrays is illustrated. The method includes positioning the object to be imaged in the x-ray imaging system, as indicated at step 802. For instance, the object is positioned between the x-ray source and the one or more XFE arrays, as in the example illustrated in FIG. 1. In some other embodiments, the one or more XFE arrays can be positioned between the x-ray source and the object, rather than between the object and the x-ray detector. Once the object has been positioned in the x-ray imaging system, one or more images are acquired, as indicated at step 804.

As indicated at step 806, a "calibration image" is provided. This calibration image depicts the locations of the x-ray focal spots generated by the XFE array for a particular ODD value, but when the object is not present in the x-ray imaging system. As an example, the calibration image may be similar to FIG. 7A. The calibration image can be provided by separately acquiring an image with the x-ray imaging system when no object is present, or can be provided by retrieving a stored calibration image that has been computationally generated based on the known properties and positioning of the XFE array.

Using the calibration image and the acquired image of the object, the displacements of the focal spots caused by the object are computed, as indicated at step 808. A refraction angle map can then be produced based on the computed displacements and the known geometries of the x-ray imaging system, as indicated at step 810. The refraction angle map, which is calculated from the displacement of the focal spots, is indicative of an electron density distribution in the object. For instance, the refraction angle map can be related to the projection of electron density distribution onto the image plane along the propagation direction of each x-ray. In order to obtain the three-dimensional distribution of electron density, a backprojection technique can be used, similar to CT imaging. For instance, multiple refraction angle maps can be acquired while changing the relative angle between the object and the imaging chain of the x-ray imaging system. In some embodiments, the relative angle is changed by rotating the object in the x-ray imaging system. In some other embodiments, the relative angle is changed by rotating the imaging chain of the x-ray imaging system about the object, similar to conventional tomographic imaging techniques. In this case, the calibration image is acquired once before all the measurements and is used for all the subsequent measurements.

Thus, from the one or more refraction angle maps, the electron density distribution in the object can be produced, as indicated at step 812. For instance, the refraction angle value can be related to the phase delay at each point by Eqn. (3), which can then be related to the projection of the real component, $\delta$, of the refractive index, n, using Eqn. (2). From multiple refraction angle maps acquired for varying projections of the object (e.g., by changing the relative orientation between the object and the imaging chain of the x-ray imaging system), the distribution of $\delta$ in the object can be obtained. Finally, the distribution of $\delta$ can be related to the electron density, $\rho_e$, using a relationship such as the following:

$$\delta = \frac{r_e \lambda^2 \rho_e}{2\pi}; \qquad (4)$$

where $r_e = 2.818 \times 10^{-15}$ m is the classical radius of the electron.

Diffractive optical components, such as the x-ray focusing elements described above and with respect to FIGS. 2-4, typically have a chromatic aberration that will result in x-rays of different energies being focused on different focal depths. It is worth noting that the XFEs can be designed to minimize chromatic aberration so as to be used with a broadband source. On the other hand, this chromatic aberration can be used for multi-spectral imaging. For instance, x-ray beams of different energies will be focused on different focal planes that are positioned at different distances from the object.

Figure 9A:
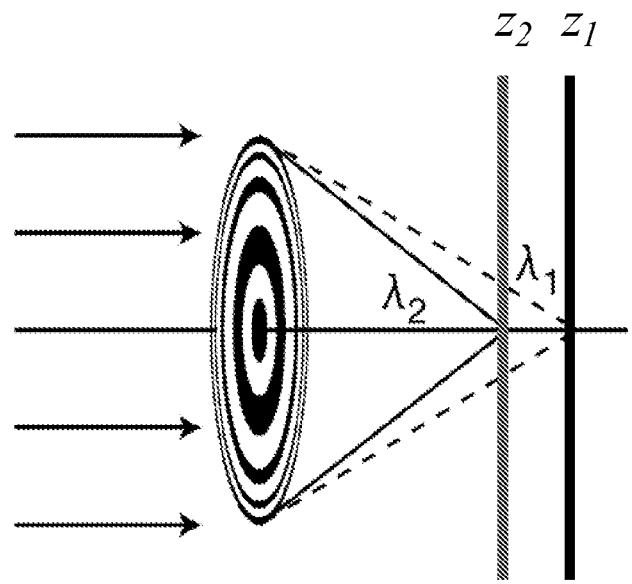
FIG. 9A is a schematic illustration of how the chromatic aberration of an XFE can be used to achieve multi-spectral phase contrast imaging.
Figure 9B:
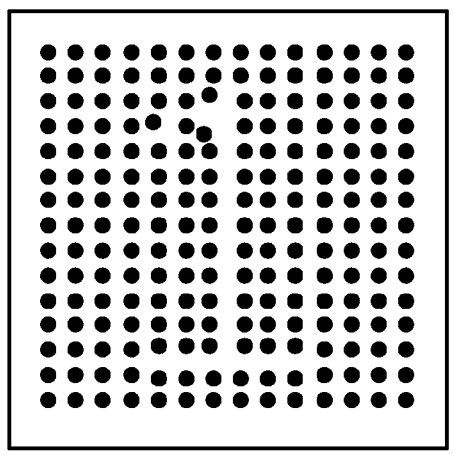
FIG. 9B is an illustrative example of an image depicting displaced x-ray focal spots associated with a first x-ray energy level at a first focal plane.
Figure 9C:
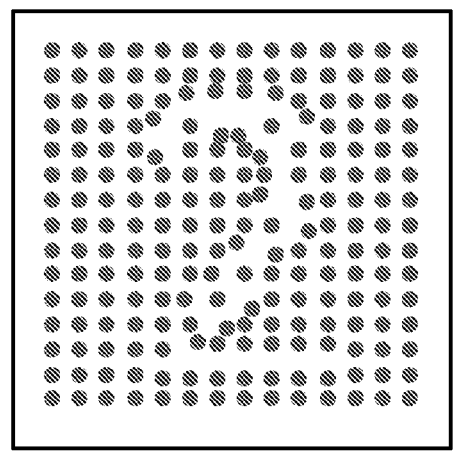
FIG. 9C is an illustrative example of an image depicting displaced x-ray focal spots associated with a second x-ray energy level at a second focal plane.

Referring to the example illustrated in FIG. 9A, x-ray beams of a first energy associated with x-rays having wavelength $\lambda_1$ are focused by an XFE on a first focal plane located at position $z_1$. In this same example, x-ray beams of a second energy that is different from the first energy, are associated with x-rays having a second wavelength $\lambda_2 \neq \lambda_1$. Because these x-rays have a different wavelength, the chromatic aberration in the XFE will focus them on a second focal plane that is located at a different position $z_2$. Thus, when the x-ray detector is placed at the position of the first focal plane a displacement image such as the one in FIG. 9B can be acquired, and when the x-ray detector is placed at the position of the second focal plane a displacement image such as the one in FIG. 9C can be acquired. From these two different images, two phase contrast images of the object can be generated, one for each of the two different energy levels.

The chromatic aberration in the XFEs can thus be exploited to achieve multi-spectral imaging. In some embodiments, multi-spectral imaging can be achieved by sweeping the detector through a plurality of different object-to-detector distances to record the focal spot displacement patterns at multiple locations. By recording the displacement patterns at these multiple locations of detector, it is possible to obtain multi-spectral x-ray phase images. In some other embodiments, multi-spectral imaging can be achieved by varying the peak voltage of an x-ray source in order to record the focal spot displacement at multiple different peak voltages for a fixed object-to-detector distance.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for x-ray phase contrast imaging using an x-ray imaging system, the steps of the method comprising:
    a) acquiring an image of an object using an x-ray imaging system that comprises:
        an x-ray source;
        an x-ray detector; and
        an array of x-ray focusing elements positioned between the x-ray source and the x-ray detector and configured to focus x-rays incident on the array of x-ray focusing elements onto a pattern of focal spots on the x-ray detector;
        wherein the acquired image is indicative of a displacement of the focal spots based on a refraction of the x-rays by the object;
    b) providing a calibration image that depicts the pattern of focal spots defined by the array of x-ray focusing elements;
    c) producing a refraction angle map that indicates a refraction angle associated with each focal spot, the refraction angle map being based on the displacement of the focal spots measured using the acquired image and the calibration image; and
    d) repeating step c) while changing a relative angle between the x-ray imaging system and the object to obtain refraction angle maps for varying angles of illumination of x-rays onto the object;
    e) producing an image of the object that is indicative of an electron density distribution in the object based on the refraction angle maps.

2. The method as recited in claim 1, wherein the array of x-ray focusing elements comprises a zone-plate array.

3. The method as recited in claim 1, wherein the array of x-ray focusing elements comprises a first array of x-ray focusing elements and a second array of x-ray focusing elements.

4. The method as recited in claim 3, wherein the first array of x-ray focusing elements is a zone-plate array comprising a plurality of horizontally-aligned linear zones and the second array of x-ray focusing elements is a zone-plate array comprising a plurality of vertically-aligned linear zones.

5. The method as recited in claim 1, wherein the array of x-ray focusing elements comprises an array of photon sieves.

6. The method as recited in claim 1, wherein providing the calibration image in step b) includes acquiring an image with the x-ray imaging system while no object is present in the x-ray imaging system.

7. The method as recited in claim 1, wherein the calibration image is computed based on known characteristics of the array of x-ray focusing elements and geometry of the x-ray imaging system.

8. The method as recited in claim 1, wherein step c) includes calculating the displacement of each focal spot in the acquired image from a location of a corresponding focal spot in the calibration image, and estimating the refraction angle associated with each focal spot based on the respective calculated displacement.

9. The method as recited in claim 1, wherein computing the electron density in step d) includes estimating phase shifts values from the estimated refraction angles, and relating the estimated phase shift values to the electron density in the object.

10. The method as recited in claim 1, wherein the array of x-ray focusing elements is an array of absorption-type x-ray focusing elements that are each composed of a high-Z material deposited on a substrate.

11. The method as recited in claim 1, wherein the array of x-ray focusing elements is an array of phase-type x-ray focusing elements that are each composed of a low-Z material deposited on a substrate.

12. The method as recited in claim 1, wherein the array of x-ray focusing elements is an array of phase-type x-ray focusing elements that are each composed by etching an x-ray focusing element pattern on a substrate.

13. The method as recited in claim 1, wherein the array of x-ray focusing elements comprises multiple sub-units of x-ray focusing elements arranged in a mosaic pattern.

14. The method as recited in claim 1, wherein step c) is repeated a plurality of times while sweeping a peak voltage of the x-ray source through a plurality of different peak voltage values in order to measure focal spot displacement patterns at the plurality of different peak voltage values for a fixed object-to-detector distance.

15. The method as recited in claim 14, wherein step d) includes producing multi-spectral images based on the focal spot displacement patterns at the plurality of different peak voltage values.

16. The method as recited in claim 1, wherein step c) is repeated a plurality of times while sweeping the detector through a plurality of different focal planes with a fixed x-ray source peak voltage in order to measure focal spot displacement patterns at the plurality of different focal planes.

17. The method as recited in claim 16, wherein step d) includes producing multi-spectral images based on the focal spot displacement patterns at the plurality of different focal planes.

18. The method as recited in claim 1, wherein the relative angle between the x-ray imaging system and the object is changed in step d) by rotating the object in the x-ray imaging system.

19. The method as recited in claim 1, wherein the relative angle between the x-ray imaging system and the object is changed in step d) by rotating the x-ray imaging system about the object.

20. The method as recited in claim 1, wherein step e) includes producing the image of the object using a back-projection.

21. The method as recited in claim 1, wherein the object is positioned between the x-ray source and the array of x-ray focusing elements in step a).

22. The method as recited in claim 1, wherein the object is positioned between the array of x-ray focusing elements and the x-ray detector in step a).

23. The method as recited in claim 1, wherein the array of x-ray focusing elements comprises at least one crystalline silicon wafer having inter-plane distances matched with wavelengths of x-rays generated by the x-ray source.

24. A method for multi-spectral x-ray phase contrast imaging using an x-ray imaging system, the steps of the method comprising:
  a) positioning an x-ray imaging system in a first position associated with a first focal plane, the x-ray imaging system comprising:
    an x-ray source that emits x-rays at a plurality of different energy levels;
    an x-ray detector; and
    an array of x-ray focusing elements (XFEs) positioned between the x-ray source and the x-ray detector, the array of XFEs being configured to focus x-rays incident on the array of XFEs onto a pattern of focal spots on the x-ray detector, the array of x-ray focusing elements having a chromatic aberration such that x-rays having a first energy are focused on the first focal plane and x-rays having a second energy are focused on a second focal plane that is different from the first focal plane;
  b) acquiring a first image of an object using the x-ray imaging system, the first image being indicative of a displacement of the focal spots on the first focal plane based on a refraction of the x-rays having the first energy by the object;
  c) adjusting the x-ray imaging system into a second position associated with the second focal plane;
  d) acquiring a second image of an object using the x-ray imaging system, the second image being indicative of a displacement of the focal spots on the second focal plane based on a refraction of the x-rays having the second energy by the object;
  e) providing a calibration image that depicts the pattern of focal spots defined by the array of x-ray focusing elements;
  f) producing a first refraction angle map based on the displacement of the focal spots on the first focal plane in the first image relative to the pattern of focal spots in the provided calibration image, the first refraction map indicating a refraction angle associated with each focal spot in the first image;
  g) producing a second refraction angle map based on the displacement of the focal spots on the second focal plane in the second image relative to the pattern of focal spots in the provided calibration image, the second refraction map indicating a refraction angle associated with each focal spot in the second image;
  h) producing a first phase contrast image from the first refraction angle map and a second phase contrast image from the second refraction angle map, wherein the first phase contrast image indicates an electron density distribution associated with the first energy and the second phase contrast image indicates an electron density distribution associated with the second energy.

\* \* \* \* \*